US00PP37564P2

(12) United States Plant Patent
Yamada

(10) Patent No.: US PP37,564 P2
(45) Date of Patent: Aug. 4, 2026

(54) ***EPIPREMNUM* PLANT NAMED 'YAMLEMJO'**

(50) Latin Name: ***Epipremnum pinnatum* (L.) Engl**
Varietal Denomination: YAMLEMJO

(71) Applicant: YAMADA NURSERIES, INC., Hiroshima (JP)

(72) Inventor: Hiroko Yamada, Hiroshima (JP)

(73) Assignee: Yamada Nurseries, Inc., Hiroshima (JP)

( * ) Notice: Subject to any disclaimer, the term of this patent is extended or adjusted under 35 U.S.C. 154(b) by 0 days.

(21) Appl. No.: 19/322,478

(22) Filed: Sep. 8, 2025

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
CPC ..... A01H 5/12; A01H 5/00; A01H 6/10
See application file for complete search history.

(56) References Cited

U.S. PATENT DOCUMENTS

PP19,965 P2 * 4/2009 Hansoti ..... A01H 6/00 Plt./373

OTHER PUBLICATIONS

Community Plant Variety Office Application Consultation version 4.25.1 retrieved on Jan. 22, 2026 at https://online.plantvarieties.eu/publicConsultation Details?registerId=20251930&denomination=yamlemjo, 2 pp. (Year: 2026).*

* cited by examiner

*Primary Examiner* — June Hwu
(74) *Attorney, Agent, or Firm* — James R. Holm; Plant Novelty Rights, LLC

(57) ABSTRACT

A new and distinct *Epipremnum* plant named 'YAMLEMJO' particularly distinguished by uniquely variegated, cordate to ovate shaped leaves with a smooth, glossy texture; leaves characterized by a distinct and stable pattern of bright, creamy-white to pale yellow sectors and patches, often concentrated along the margin and mid-lateral portions on the upper surface of the leaf blade; variegation that is irregular yet consistent across the leaf blade; young leaves having irregular and blotchy dark yellow-green centers and irregularly blotched and marbled laterally and towards the margins with light yellow-green on the upper surface, while mature leaves have a higher contrast and more pronounced light yellow-green colorations laterally and towards the margins on the upper surface; and petioles that are short to medium length, smooth, and slightly lighter green than the darkest green sectors of the leaf blade.

2 Drawing Sheets

Figure 1:
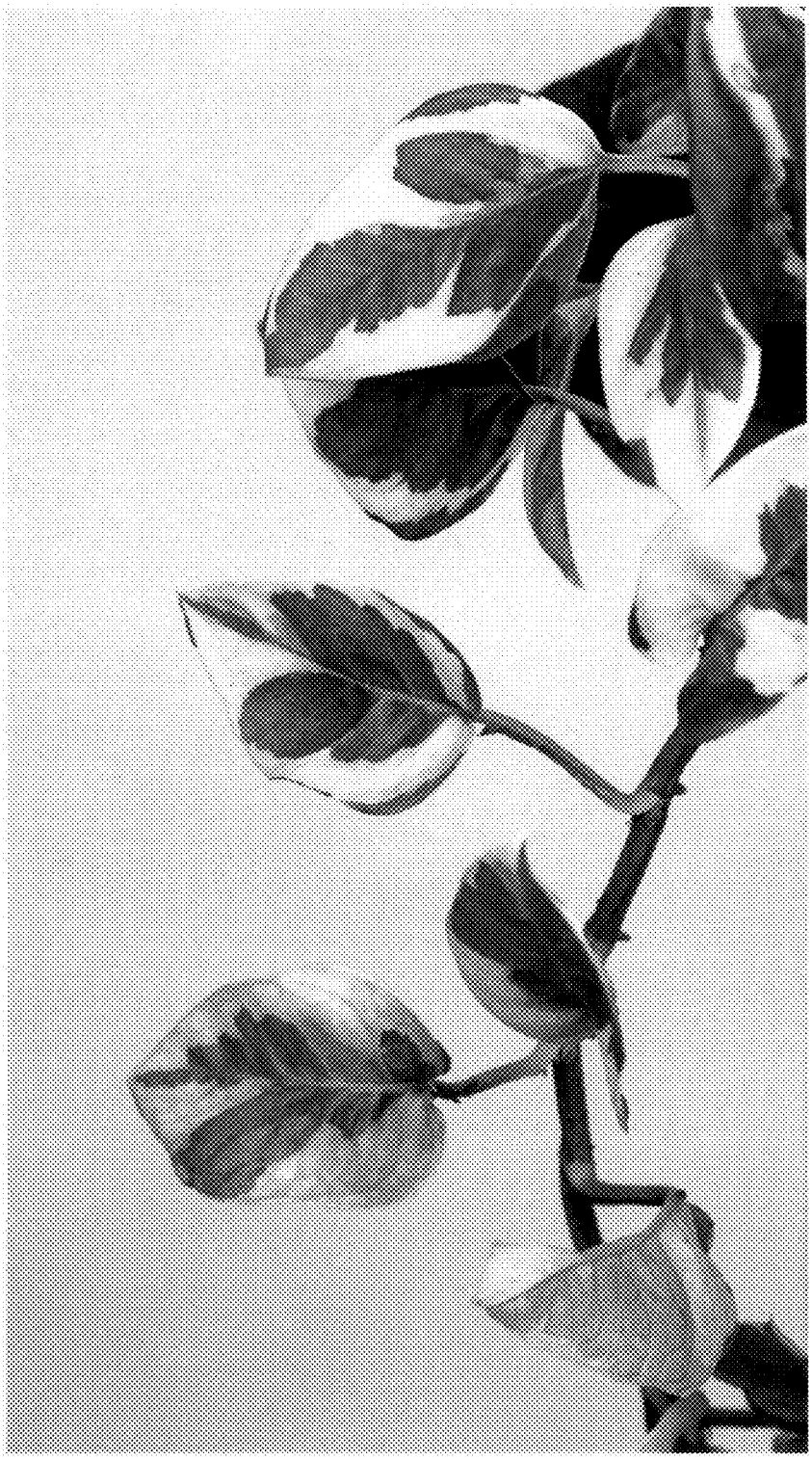

Genus and species: *Epipremnum pinnatum* (L.) Engl.
Variety denomination: 'YAMLEMJO'.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period prior to the filing date.

BACKGROUND OF THE NEW PLANT

The present invention comprises a new and distinct variety of *Epipremnum* plant, botanically known as *Epipremnum pinnatum,* and hereinafter referred to by the variety name 'YAMLEMJO'.

The new *Epipremnum* cultivar 'YAMLEMJO' is the result of a naturally occurring branch mutation of the *Epipremnum* cultivar 'Marble Queen' (unpatented). 'YAMLEMJO' was found and selected by the inventor in a nursery located in Hiroshima, Japan in October 2020. The objective was to select and reproduce *Epipremnum pinnatum* plants with prominent and unique leaf variegation and improved growing qualities, namely suitability to produce plants year-round. The new cultivar was selected as a single plant from a group of more than 100 plants representing superior clones of the parent *Epipremnum* cultivar 'Marble Queen'. Clones were selected for several years based on superior rooting performance (shorter rooting time and less plant losses during rooting), superior growth performance under lower light conditions during the months of October through March, and unique variegation.

The new *Epipremnum* cultivar was selected based on its uniquely variegated, ovate leaves with a smooth, glossy texture as well as excellent rooting ability during transpant cutting stage and excellent growth performance under low light conditions. 'YAMLEMJO' was first reproduced asexually using vegetative meristem tip cuttings in October 2020 in Hiroshima, Japan. Asexual propagation by vegetative meristem tip cuttings of the new variety has shown that the unique features of the new variety are stable and reproduced true-to-type to date through twelve successive generations.

SUMMARY OF THE INVENTION

The new *Epipremnum* cultivar 'YAMLEMJO' has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Epipremnum* cultivar. The combination of these characteristics distinguishes 'YAMLEMJO' as a new and distinct variety of *Epipremnum*.

1. Uniquely variegated, cordate to ovate shaped leaves with a smooth, glossy texture.
2. Leaves characterized by a distinct and stable pattern of bright, creamy-white to pale yellow sectors and patches, often concentrated along the margin and mid-lateral portions on the upper surface of the leaf blade.
3. Light colored leaf pigmentation that contrasts sharply with the surrounding medium to dark green areas, which may range from vivid grass-green to deep emerald.
4. Variegation that is irregular yet consistent across the leaf blade, with some leaves displaying large, nearly half-leaf creamy sectors, while others show marbled or streaked patterns.
5. Young leaves having irregular and blotchy dark yellow-green centers and irregularly blotched and marbled laterally and towards the margins with light yellow-green on the upper surface, while mature leaves have a higher contrast and more pronounced lighter yellow-green colorations laterally and towards the margins on the upper surface.
6. Leaf margins remaining uniformly green or partially infused with lighter tones.
7. Petioles that are short to medium length, smooth, and slightly lighter green than the darkest green sectors of the leaf blade.
8. Leaf arrangement that is alternate along the stem with individual leaves generally flat to slightly undulate.

The new *Epipremnum* cultivar can be distinguished from its progenitor or parent *Epipremnum* cultivar 'Marble Queen' in the following characteristics:

1. Leaves of 'YAMLEMJO' display large, well-defined, creamy-yellow to creamy-white sectors, often concentrated along the margins and mid-lateral portions of the leaf blade, and variegation in blocks rather than being finely mottled, whereas leaves of 'Marble Queen' exhibit an overall marbled variegation pattern with small, irregular white and light green flecks dispersed throughout the leaf surface.
2. Leaf variegation of 'YAMLEMJO' may have a warm, creamy-yellow hue, especially on younger leaves, in addition to the creamy-white sectors, whereas 'Marble Queen' has variegation that is consistently bright white, lacking yellowish tones.
3. Leaves of 'YAMLEMJO' have green areas that are a uniformly medium to dark green, providing a strong contrast with the lighter variegation, whereas 'Marble Queen' has green areas that are lighter and interspersed with fine flecks of white, reducing the contrast between the green coloration and the variegated sectors.
4. Leaves of 'YAMLEMJO' are broader and more ovate, with a smoother overall appearance, whereas leaves of 'Marble Queen' are generally slightly narrower and can appear more elongated with more pointed tips.
5. Leaves of 'YAMLEMJO' have a highly contrasted and bold color pattern with a clear separation between the green and variegated sectors, whereas leaves of 'Marble Queen' have a more diffuse color contrast due to the fine marbling pattern across the leaf blade.

The new *Epipremnum* cultivar can be distinguished from the related known variety of *Epipremnum* cultivar 'NJOY' (U.S. Plant Pat. No. 19,965) in the following characteristics:

1. 'YAMLEMJO' has variegation that appears as large, well-defined sectors of creamy-yellow to creamy-white, often concentrated along the margins and mid-lateral portions of the leaf blade, whereas 'NJOY' has variegation that is predominantly white to cream appearing in irregular patterns and frequently concentrated along the margins with a marbled or flecked appearance.
2. 'YAMLEMJO' exhibits variegation with a warmer tone (creamy-yellow to light chartreuse) in addition to white sectors, whereas 'NJOY' exhibits variegation that is consistently bright white without notable yellowish tones.
3. The green sectors on leaves of 'YAMLEMJO' are a deeper and more uniformly colored medium to dark green, whereas the green sectors on leaves of 'NJOY' are often a lighter green and may appear more mottled or irregular in color intensity.
4. 'YAMLEMJO' tends to have slightly broader, more ovate shaped leaves with a fuller lamina, whereas 'NJOY' has leaves that are somewhat narrower and more elongated.
5. 'YAMLEMJO' has a bolder, more contrasting leaf color pattern with fewer, yet larger blocks of color, giving it a distinct and less fragmented look compared to the finer, more speckled variegation of 'NJOY'.

DESCRIPTION OF THE PHOTOGRAPHS

This new *Epipremnum* cultivar is illustrated by the accompanying-colored photographs which show the overall appearance and distinct characteristics of the plant. The colors shown are as true as can be reasonably obtained by conventional photographic procedures. The photographs are of a 12-month-old plant grown in a 17-centimeter circular container in a conventional glass greenhouse in Rijsenhout, The Netherlands. Colors in the photographs may differ slightly from the color values cited in the botanical description which accurately describes the colors of the new variety.

FIG. 1. shows typical juvenile foliage (bottom) and mature foliage (top) observed on plants of 'YAMLEMJO'.

Figure 2:
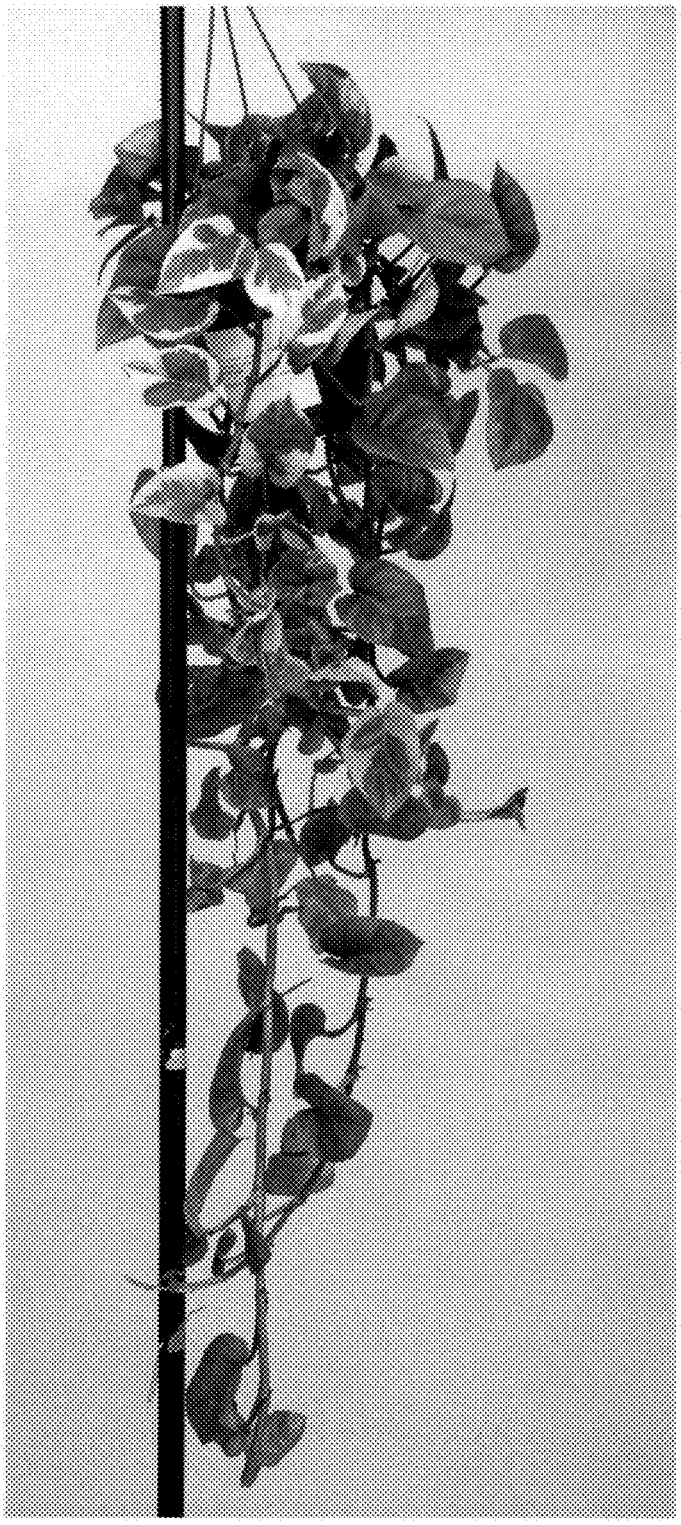

FIG. 2. shows the overall plant form and foliage of typical plants of 'YAMLEMJO'.

DESCRIPTION OF THE NEW VARIETY

In the following description, color references are made to The Royal Horticultural Society Colour Chart, Sixth Edition, except where general color terms of ordinary dictionary significance are used.

The following observations and measurements describe plants grown in a conventional glass greenhouse located in Rijsenhout, The Netherlands. Plants were grown under normal daytime light levels in Rijsenhout, The Netherlands with no artificial supplemental lighting provided. Detailed descriptions were taken in July 2025 from 12-month-old plants grown in 17-centimeter circular containers. Measurements and numerical values represent averages of typical plant types.

DETAILED BOTANICAL DESCRIPTION

Classification:

*Family*.—Araceae.

*Botanical*.—*Epipremnum pinnatum* (L.) Engl.

*Common*.—Pothos.

*Denomination*.—'YAMLEMJO'.

General description:

*Plant type*.—Tropical perennial vine for use as a potted plant.

*Approximate container size and/or cropping system*.—13.0 cm or larger pots.

*Growth habit*.—Pendulous.

*Overall plant shape*.—Broad, ovate with pendulous branches.

*Height from soil level to top of foliar plane*.—13.4 cm from the soil to the top of the foliar plane and 97.5 cm from the tips of the pendulous branches to the top of the foliar plane.

*Plant spread*.—35.9 cm.

*Growth rate*.—On average one new leaf emerges every 2 to 3 weeks and under optimal conditions (bright indirect light, warm temperatures, and healthy roots), new leaves can emerge every 1 to 2 weeks.

*Branching habit*.—Basal branching with no lateral branches present.

*Propagation type*.—Vegetative meristem tip cuttings.

*Average number of days to a rooted cutting*.—7 to 14 days to initiate roots and 3 to 5 weeks to establish a well-developed root system for transplanting.

Branch description:

*Number of main branches or stems per plant*.—Average 8.

*Number of lateral branches per plant*.—None.

*Main branch length*.—Average 54.4 cm.

*Main branch diameter*.—Average 0.5 cm.

*Main branch internode length*.—Average 3.7 cm.

*Stem appearance and shape*.—Rounded.

*Stem luster*.—Matte to very slightly glossy.

*Stem aspect/angle from vertical*.—Average 35° at soil level with pendulous branches growing downward near vertical.

*Stem strength*.—Strong.

*Stem color*.—Developing stems: Upper surface: Near a blend of 143A and 143B (yellow-green). Lower surface: Near 144D (yellow-green). Mature stems: Upper surface: Near 147A (yellow-green). Lower surface: Near 144C (yellow-green). Internodes: Upper surface: Near a blend of 147A and 147B (yellow-green). Lower surface: 144A (yellow-green).

*Pubescence*.—Not present.

*Arial roots*.—Present at nodes, average of 1.4 cm in length and 2.3 mm in diameter, non-fibrous, tough and slightly fleshy, colored near N199B (greyed-brown).

Foliage description:

*Arrangement*.—Alternate and simple.

*Quantity of foliage*.—Average of 13 leaves per stem.

*Lamina*.—Shape: Cordate to ovate. Length: Average 7.1 cm. Width: Average 5.1 cm. Aspect: Carinate. Apex shape: Acute. Base shape: Cordate and sometimes rounded. Margins: Entire, slightly coarsely undulate, slightly revolute. Texture (both upper and lower surfaces): Smooth, glabrous, slightly leathery. Pubescence: Not present. Rugosity (both upper and lower surfaces): Slightly bullate. Luster (both upper and lower surfaces): Very slightly glossy. Color: Juvenile foliage: Upper surface: An irregular and blotchy center coloration of near a blend of 138A and 147B (yellow-green) and irregularly blotched and marbled laterally and towards and near the margins with near 144A to near 144D; venation on blotched and marbled areas is darker than near 144A (yellow-green). Lower surface: Near 147C (yellow-green) and blotched and marbled with slightly lighter than near 146D (yellow-green); secondary and tertiary venation are darker, near 146A (yellow-green). Mature foliage: Upper surface: An irregular and blotchy center coloration of near NN137B (green) and 147C (yellow-green), irregularly blotched and marbled laterally and towards and near the margins with near 145A (yellow-green) and near 150D (yellow-green), and sectors of near 147C (yellow-green) on the leaf margin; upper surface of solid green leaves colored near NN137B with slight marbled tones of near 147C. Lower surface: Near 194A (greyed-green), blotched and marbled with near NN137B (yellow-green) and near 150D (yellow-green) and slightly darker; lower surface of solid green leaves colored near 147C. Venation: Pattern: Pinnate. Color (mature leaves): Upper surface: Near 146D (yellow-green). Lower surface: Near 148B (yellow-green).

*Petiole*.—Length: Average 4.4 cm. Diameter: Average 0.3 cm. Texture: Smooth, glabrous. Luster (both upper and lower surfaces): Slightly glossy. Strength: Strong. Color: Upper surface: Near 146A (yellow-green). Lower surface: Near 146B (yellow-green).

*Petiole wings*.—Length: Average 3.6 cm. Width: Average 0.2 cm. Color (both upper and lower surfaces): Near N199B (greyed-brown), darker towards the distal end, near 200A (reddish brown).

Inflorescence: None observed to date.

Heat tolerance: At least tolerant to temperatures up to 40 degrees Celsius.

Cold tolerance: At least hardy to USDA zone 10.

USDA hardiness zones: Zones 10 to 13.

Rain tolerance: Moderate.

Wind tolerance: Low to Moderate.

Disease and pest tolerance: No claims are made to any superior disease or insect resistance or tolerance.

What is claimed is:

1. A new and distinct cultivar of *Epipremnum* plant named 'YAMLEMJO' as illustrated and described herein.

* * * * *